(12) United States Patent
Spariosu et al.

(10) Patent No.: US 9,440,289 B1
(45) Date of Patent: Sep. 13, 2016

(54) METHOD AND APPARATUS FOR X-RAY LASER INTERROGATION

(71) Applicant: Raytheon Company, Waltham, MA (US)

(72) Inventors: Kalin Spariosu, Thousand Oaks, CA (US); James A. Wurzbach, San Diego, CA (US)

(73) Assignee: Raytheon Company, Waltham, MA (US)

( * ) Notice: Subject to any disclaimer, the term of this patent is extended or adjusted under 35 U.S.C. 154(b) by 49 days.

(21) Appl. No.: 13/650,368

(22) Filed: Oct. 12, 2012

(51) Int. Cl.
*G01N 23/203* (2006.01)
*B22F 9/00* (2006.01)

(52) U.S. Cl.
CPC ........................................ *B22F 9/00* (2013.01)

(58) Field of Classification Search
USPC .......................................................... 378/70
See application file for complete search history.

(56) References Cited

U.S. PATENT DOCUMENTS

| | | | |
|---|---|---|---|
| 4,229,708 A * | 10/1980 | Mani | H01S 4/00 372/21 |
| 5,206,592 A | 4/1993 | Buess et al. | |
| 5,524,133 A | 6/1996 | Neale et al. | |
| 5,574,284 A | 11/1996 | Farr | |
| 5,600,303 A | 2/1997 | Husseiny et al. | |
| 5,642,393 A | 6/1997 | Krug et al. | |
| 5,692,029 A | 11/1997 | Husseiny et al. | |
| 5,958,299 A | 9/1999 | Kury et al. | |
| 5,974,111 A | 10/1999 | Krug et al. | |
| 6,392,747 B1 * | 5/2002 | Allen | G01S 7/4802 356/141.1 |
| 6,661,876 B2 | 12/2003 | Turner et al. | |
| 7,023,956 B2 | 4/2006 | Heaton et al. | |
| 7,161,150 B2 | 1/2007 | Frankle et al. | |
| 7,202,776 B2 * | 4/2007 | Breed | 340/435 |
| 7,453,987 B1 * | 11/2008 | Richardson | 378/98.9 |
| 7,607,338 B1 | 10/2009 | Lewis et al. | |
| 7,693,262 B2 | 4/2010 | Bertozzi et al. | |
| 8,411,820 B1 * | 4/2013 | Browder | G01N 24/084 378/43 |
| 8,582,720 B2 * | 11/2013 | Morton | G01V 5/0008 378/57 |
| 2005/0276753 A1 * | 12/2005 | Scott et al. | 424/1.11 |
| 2006/0262901 A1 | 11/2006 | Heaton et al. | |
| 2007/0098142 A1 * | 5/2007 | Rothschild | G01N 23/04 378/57 |
| 2007/0241283 A1 | 10/2007 | Chu et al. | |
| 2009/0290680 A1 | 11/2009 | Turner et al. | |
| 2009/0304152 A1 * | 12/2009 | Adamski et al. | 378/64 |
| 2010/0006769 A1 | 1/2010 | Kraft et al. | |

OTHER PUBLICATIONS

Nebbia et al., "Detection of Buried Landmines and Hidden Explosives Using Neutron, X-ray and Gamma-ray Probes", Europhysics News, Jul./Aug. 2005, pp. 119-123.
Csikai et al., "Investigations on Landmine Detection by Neutron-based Techniques", Applied Radiation and Isotopes 61 (2004) 11-20, Elsevier, Feb. 2004, pp. 11-20.

(Continued)

*Primary Examiner* — Phillip A Johnston
(74) *Attorney, Agent, or Firm* — Daly, Crowley, Mofford & Durkee, LLP

(57) ABSTRACT

Methods and apparatus for a stand-off interrogation system having an ultra-fast X-ray source (incoherent and/or X-ray laser) with an ultra-short pulse emission to irradiate a target material behind a barrier. In one embodiment, the target material is an explosive material in a container. The composition of the target material is directly determined from the detected elemental differential back-scattering signatures.

20 Claims, 14 Drawing Sheets

(56) References Cited

OTHER PUBLICATIONS

D'Angelo, A., "Review of Compton Scattering Projects", INFN Roma II, Via della Ricerca Scientifica, 1 I-00133 Rome Italy, Jun. 1998, 5 pages.
Chen et al., "An X-ray Source Based on Compton Backscattering of $CO_2$ Laser and 100 MeV Electrons", Science Direct, Nuclear Instruments and Methods in Physics Research A 580 (2007) 1184-1190, 7 pages.
Standoff Explosives Detection System (SEDS), Raytheon Company, Apr. 28, 2011, 1 page.
DD 109 Neutron Generator, Adelphi Technology Inc., Raytheon Company, Apr. 28, 2011, 1 page.
Mobile High-Energy X-ray Cargo and Vehicle Inspection Systems for U.S. Customs and Border Protection, Homeland Security News, Homeland Security/Defense Industry briefs, Raytheon Company, Apr. 25, 2011, 1 page.
Air Cargo Screening with Gemini™ Parcel Inspection Systems, Raytheon Company, Apr. 28, 2011, 1 page.
TaraView, Explosives Detection System, Raytheon Company, Apr. 28, 2011, 1 page.
TeraView Explosive Detection, Detection of Explosives and Materials Characterization, Raytheon Company, Apr. 28, 2011, 1 page.
Measurement Technologies, Engineering At LLNL, Terahertz Spectroscopic Imaging for Standoff Detection of High Explosives, Raytheon Company, Apr. 28, 2011, 1 page.
Portendo Technology, Raman, Raytheon Company, Apr. 28, 2011, 1 page.

* cited by examiner

Elemental Composition
Percent by Weight (Percent by weight and atomic percent are related, but different)

| | H | C | N | O | Na | Al | Si | K | P | Ca | Fe | |
|---|---|---|---|---|---|---|---|---|---|---|---|---|
| ANFO | 6 | 5 | 33 | 56 | | | | | | | | By calculation: 94% ammonium nitrate, 6% fuel oil H 5.6%, C 5.1%, N 32.9%, O 56.4% |
| Wood | ~6 | ~50 | ~0 | ~44 | | | | | | | | Overall average spanning multiple woods and sources Roger C. Petterson, *The Chemical Composition of Wood*, Chap 2 http://www.fpl.fs.fed.us/documnts/pdf1984/pette84a.pdf |
| C4 | 4 | 22 | 34 | 40 | | | | | | | | By Calculation: 91% RDX, 5.3% 2-ethyl hexyl sebacate, 2.1% polyisobutylene, 1.6% fuel oil http://en.wikipedia.org/wiki/C-4_(explosive) |
| Human Body | 10 | 18 | 3 | 65 | 0.15 | | 0.000006 | 0.002 | 0.25 | 1.1 | 1.4 | 0.006 | 65%–90% of cell mass is water 99% is oxygen, carbon, hydrogen, nitrogen, calcium, and phosphorus 0.85% is potassium, sulfer, sodium, chlorine, and magnesium 0.15% trace elements http://en.wikipedia.org/wiki/Composition_of_the_human_body |
| Granite | | | | 49 | 2.7 | | 34 | 3.4 | 0.05 | 1.3 | 2.2 | Global average derived from 2485 samples http://en.wikipedia.org/wiki/Granite |

FIG. 5

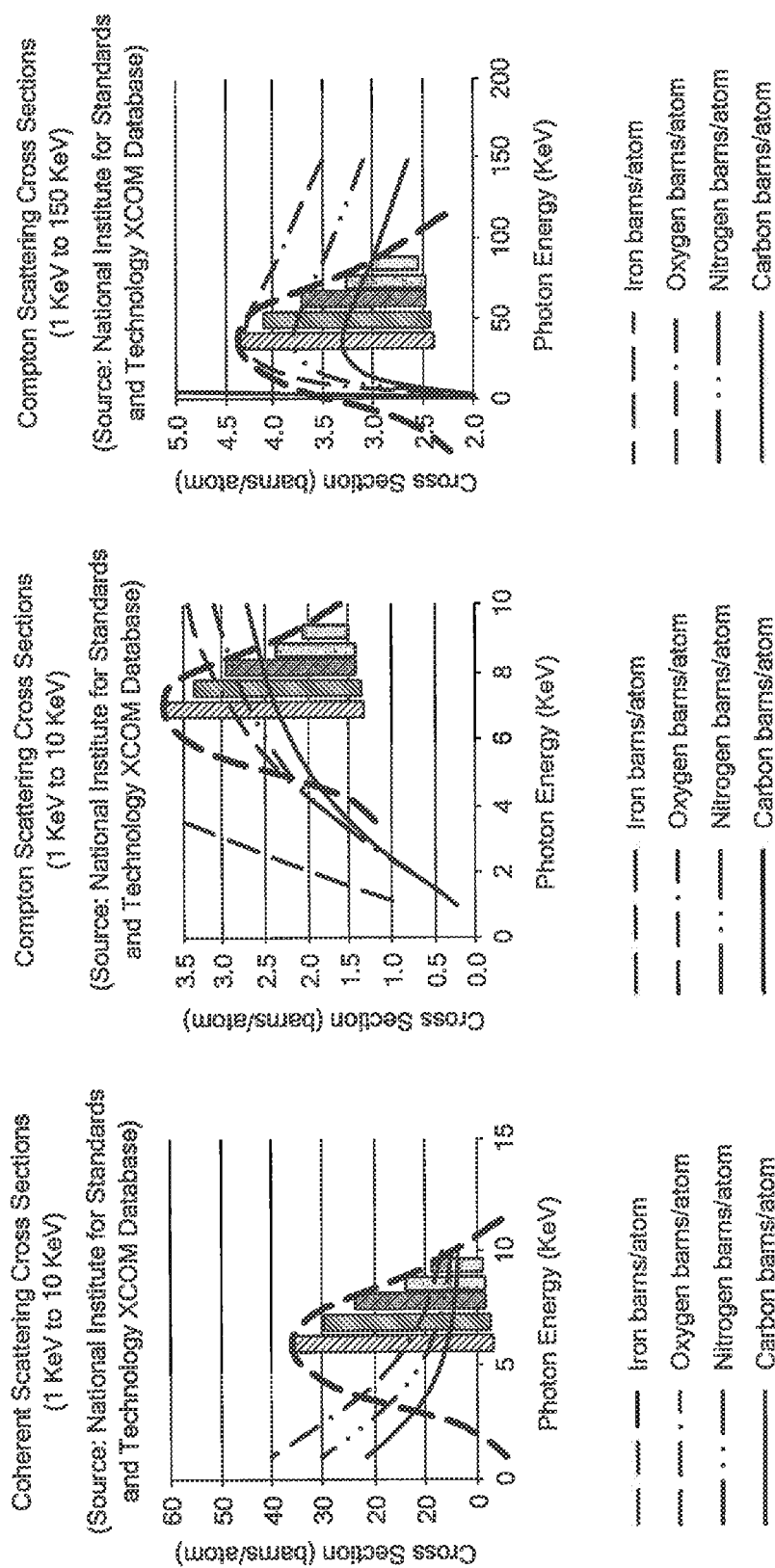

METHOD AND APPARATUS FOR X-RAY LASER INTERROGATION

BACKGROUND

There are a variety of known active interrogation systems directing some type of energy at a target to attempt to identify materials in the target. Laser induced active sensing techniques such as fluorescence, Raman, and multi/hyper spectral analysis generally have limited ability to penetrate into the bulk of target materials. Another system uses nuclear activation via a neutron beam to activate substances, which creates significant safety issues based on radiation.

They are usually employed to interrogate the outside surface of a target material. Some interrogation systems use energy having TeraHertz frequencies, which are limited to very short range applications, such as less than one meter. Nuclear quadrupole magnetic resonance imaging systems can detect explosives, but are subject to defeat by simple RF shielding. While standoff detection systems above may have some practical utility, each has certain limitations and/or safety issues in various applications. The most sensitive techniques are well suited to trace or residue detection on an exterior surface. Passive EO techniques have also been employed for residue detection. Raman inspection systems are sensitive and can in principle operate at larger stand-off ranges, however, they are still limited to detection of the residues only and not bulk materials detection inside a container or targets of interest typically in a container or behind a barrier.

Conventional X-ray sensors can penetrate containers for indirect interrogation of suspect explosive and contraband materials concealed within. One type of X-ray backscatter system utilizes broad, incoherent, CW X-ray energy to classify target materials by density maps/differences. Other X-ray sensor systems operate in a transmission mode, and yet other standoff x-ray/γ-ray sensors utilize Compton backscattering and/or induced fluorescence to detect materials. In most examples, the results are shown in a two-dimensional output, such as a computer display, a radiograph/photograph, or similar. All information related to a profile of the target material as a function of its thickness or depth is lost, having been collapsed into the two-dimensional output.

In some cases, the constraint of a two-dimensional output can defeat the purpose of the X-ray examination. When the target material is enclosed within a container, returns derived from the container walls and atmospheric scattering contributions are collected as components of the two-dimensional output. In that case, interference from the container wall and atmosphere at least obscures the output, and it may dominate the output, such that any signal from the target material inside is overwhelmed. This problem will persist in the absence of a practical method to separate the signal of the target material from that of the container walls and atmospheric scattering.

Efforts to capture X-ray data as a function of thickness or depth generally resort to some form of tomography, in which the target material is viewed from more than one angle. In some examples, a single X-ray source and a single detector might be aligned to capture data at one angle, and then translated to capture more data at one or more additional angles in a serial sequence. In other examples, arrays of multiple X-ray sources and/or multiple detectors might be invoked to capture data at multiple angles simultaneously. A structure, such as a goniometer, might be included to facilitate reproducible translation of the source(s) and/or detector(s). In all of these cases, however, compromises are required in order to capture a three-dimensional profile. More time might be required (as in the example of a serial sequence), or there might be more exposure to radiation (as a result of multiple exposures in a serial sequence or from an array of multiple sources), or additional space might be required (to accommodate an array of sources and/or detectors), or additional complexity and expense might be imposed (for a goniometer and/or any related structure), or some combination of these factors. These compromises derive from the fact that current, conventional, state-of-the-art X-ray sensor systems are broad band and incoherent, and more significantly, they are either true CW or quasi CW with long pulse emission.

CW systems are also susceptible to increased background due to atmospheric scattering of the X-ray beam because the detector continually integrates the signal. Lacking a convenient mechanism for separating the signal of the target from radiation randomly scattered off the atmosphere, conventional X-ray systems include a random background that obscures the output.

Conventional X-ray sources such as those derived from X-ray tubes provide for a spatially divergent X-ray beam for which intensity falls off rapidly with distance. Accelerators (synchrotron for example) can provide collimated beams but with a sizeable complexity associated with such system. A collimated beam can be formed with a collimator. In the approach described here, we propose the use of an ultra-fast X-ray source such as that derived from a table-top X-ray laser and/or an ultra-fast laser initiated/driven X-ray tube (with appropriate collimating x-ray optics) which enables range gated characterization of a target material is achieved at standoff ranges.

SUMMARY

The present invention provides methods and apparatus for stand-off interrogation to provide chemical composition detection and identification using ultra-fast X-ray sources including x-ray lasers. With this arrangement, materials of interest, such as explosives, in sealed containers can be identified. While exemplary embodiments of the invention are shown and described in conjunction with illustrative applications and configurations, it is understood that embodiments of the invention are applicable to inspection systems in general in which it is desirable to identify the composition of a material in a container or behind a barrier or buried underground.

In one aspect of the invention, a system comprises an ultra-fast X-ray source (incoherent and/or X-ray laser) with an ultra-short pulse emission for the illumination of a target, a gated detector to detect one or more X-ray photons emitted from the target, or transmitted through the target, as a result of illumination of the target by the photon source, and a signal processor coupled to the detector to analyze the detected photons, for characterizing a material forming at least part of the target.

The system can further include one or more of the following features: the signal processor is configured to identify the material as comprising an explosive material, photon energies from the photon source are at least 5 keV (kilo electron Volts), photon pulses from the photon source have pulse durations less than 10 picoseconds, the photon source is either based upon high harmonic generation to generate highly directional low divergence coherent x-ray laser beams, or an ultra fast triggered incoherent pulse x-ray source, the target is located behind a barrier, the target is within a container, the photons are emitted from the material due to reflection, refraction, Compton scattering, coherent scattering, and/or fluorescence, at least some of the photons from the photon source are transmitted through the material, the detector is fixed on or immediately adjacent to the photon source to provide a monostatic LADAR configuration, the detector is fixed at a location that is remote from the source to provide a bistatic/multistatic LADAR configuration, the detector is movable, the signal processor is configured to perform range gating on the detector output for isolating signal return from the target and/or enabling three dimensional mapping/imaging of the target, a beam from the photon source is directed at a specific location on the target for spot interrogation at a standoff distance, and/or a beam from the photon source is scanned to interrogate a target area.

In another aspect of the invention, a method comprises: directing an ultra-fast X-ray source (incoherent and/or X-ray laser) with an ultra-short pulse emission to illuminate a target, detecting one or more of photons, electrons and/or positrons emitted from the target, or transmitted through the target, as a result of illumination of the target by the photon source, and analyzing the detected photons, for characterizing a material forming at least part of the target. The system can further include identifying the material as comprising an explosive material and/or the photon energies from the photon source are at least 5 keV (kilo electron Volts) and/or photon pulses from the photon source have pulse durations less than 10 picoseconds.

BRIEF DESCRIPTION OF THE DRAWINGS

The foregoing features of this invention, as well as the invention itself, may be more fully understood from the following description of the drawings in which:

FIG. 5 is a tabular representation of the elemental composition of exemplary materials at least some of which can be detected by an ultra-fast X-ray source (incoherent and/or X-ray laser) interrogation system in accordance with exemplary embodiments of the invention;

FIGS. 7A-C show coherent scattering cross sections for certain materials;

DETAILED DESCRIPTION

Figure 1:
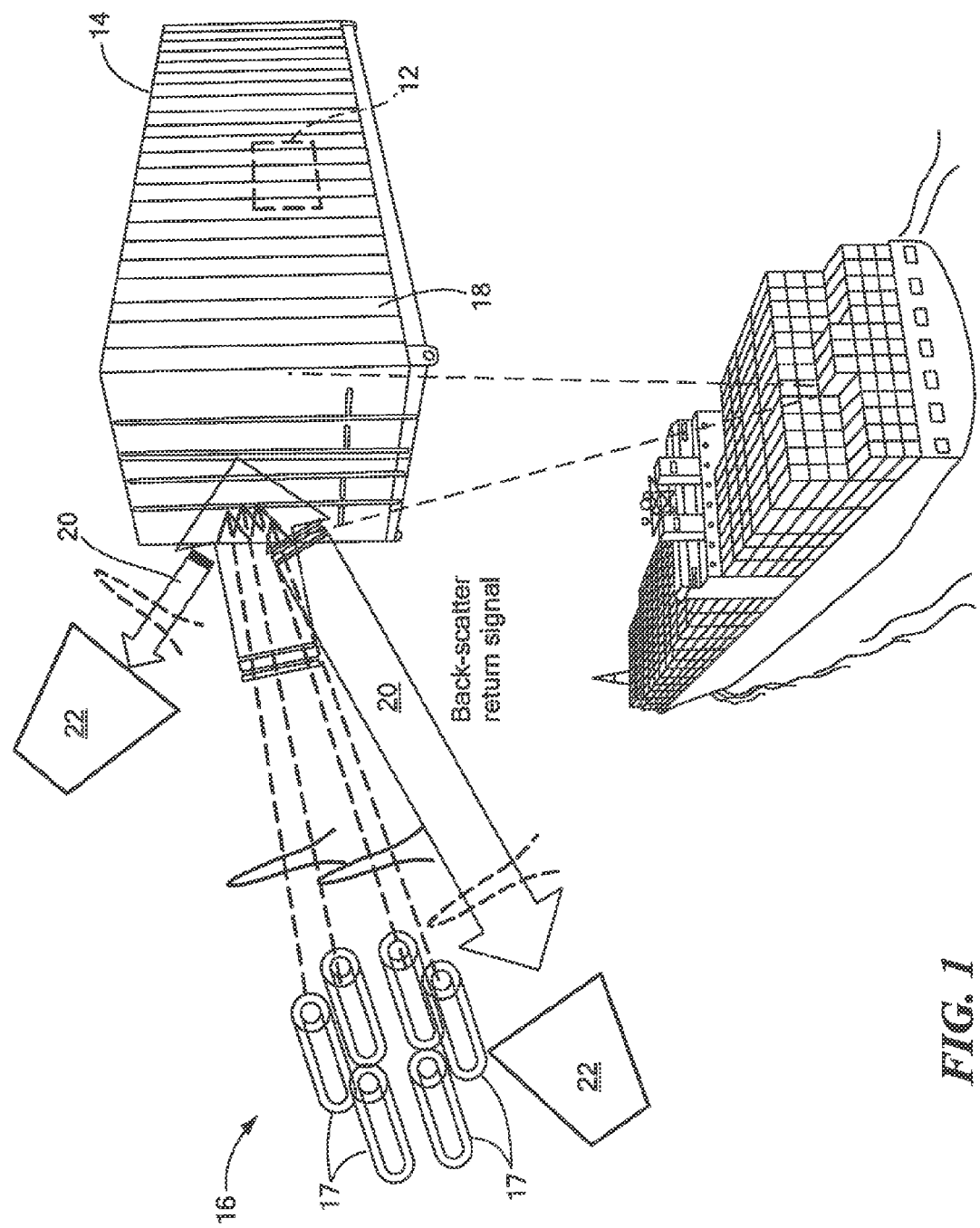
FIG. 1 is a schematic representation of an exemplary ultra-fast X-ray source (incoherent and/or x-ray laser) interrogation system in accordance with exemplary embodiments of the invention.

FIG. 1 shows an exemplary system 10 to detect a material 12 within a container 14, such as a shipping container, or behind a barrier. An energetic ultra-fast X-ray source (incoherent and/or X-ray laser) 16 (10 keV to >100 keV) generates photon energy that can penetrate container walls 18 and interrogate the interior to detect and identify the material 12, e.g., bulk explosive, directly, in contrast with inferring the presence of an explosive from a surface residue as in conventional systems. The pulsed X-ray source 16 can be frequency agile, meaning that it can generate different mean energy pulsed X-ray emission profiles/outputs. Alternatively, the pulsed X-ray source 16 can be constructed with a multiplicity of transmitter modules 17, each of which produces a different photon energy or mean photon energy. Backscatter return signal 20 is received by energy resolving X-ray detectors 22 in mono-static and/or bi-static configurations.

Ultra short pulse X-ray sources enable range gating, which produces a 3D mapping of targets of interest. Two dimensional (x-y or angle-angle) is achieved via a scanning approach. The third (depth or range) dimension is enabled via range gating the return signals. This can then provide signal detection by the detectors 22 from selected depth beyond the container 14 wall in order to pin point a suspect bulk material inside said container. It is understood that detection can include one or more of photons, emitted from the target, or transmitted through the target, as a result of illumination of the target by the photon source.

Figure 2:
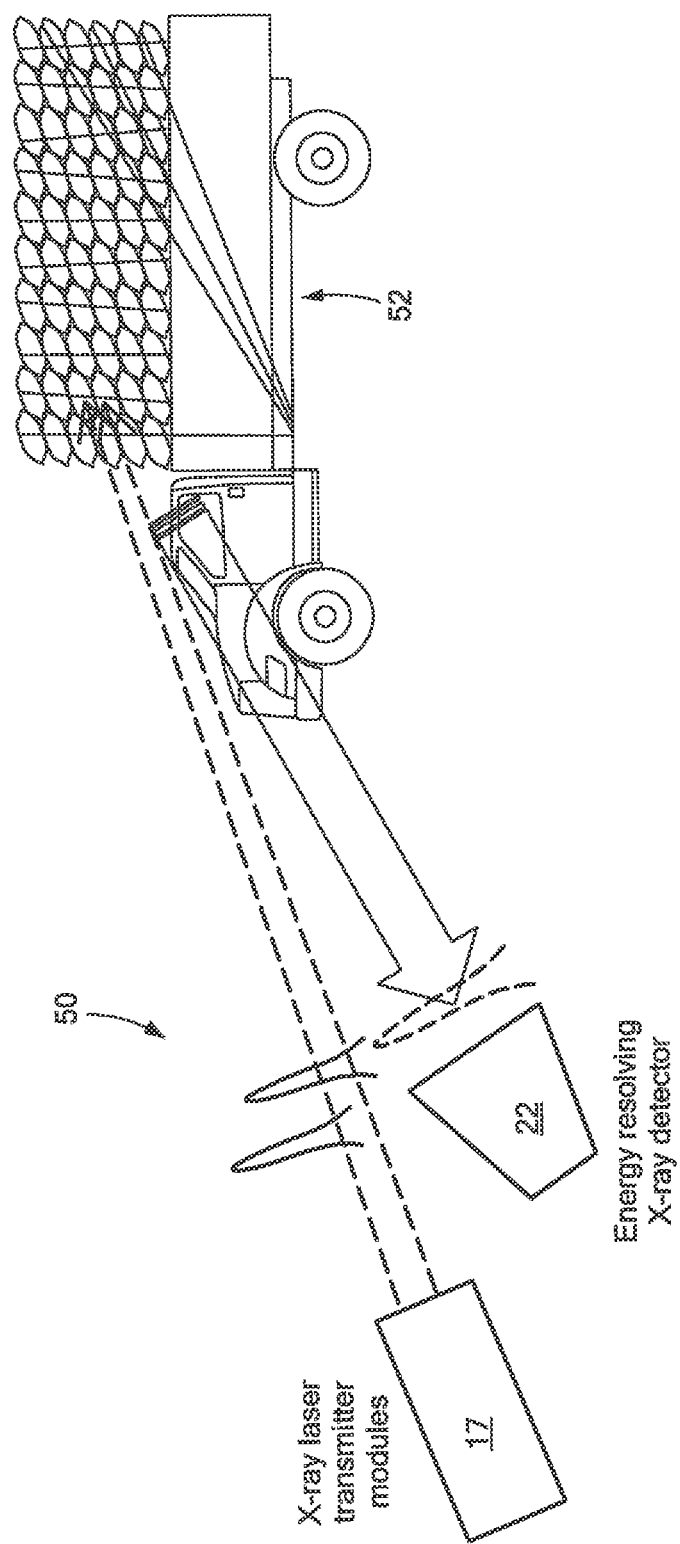
FIG. 2 is a schematic representation of a further exemplary ultra-fast X-ray source (incoherent and/or x-ray laser) interrogation system in accordance with exemplary embodiments of the invention.

FIG. 2 shows a further ultra-fast X-ray source (incoherent and/or X-ray laser) interrogation system 50 for a checkpoint to interrogate vehicles 52 for determining if a load carried by the vehicle is benign, such as sacks of cement, or contraband, such as Ammonium Nitrate or other explosives/contraband. X-ray transmitter modules 17 direct range-gated energy pulses at the vehicle 52 and detectors 22 receive energy from the target, including any contraband materials. Exemplary implementations can include bi-static and/or mono-static configurations.

Figure 3:
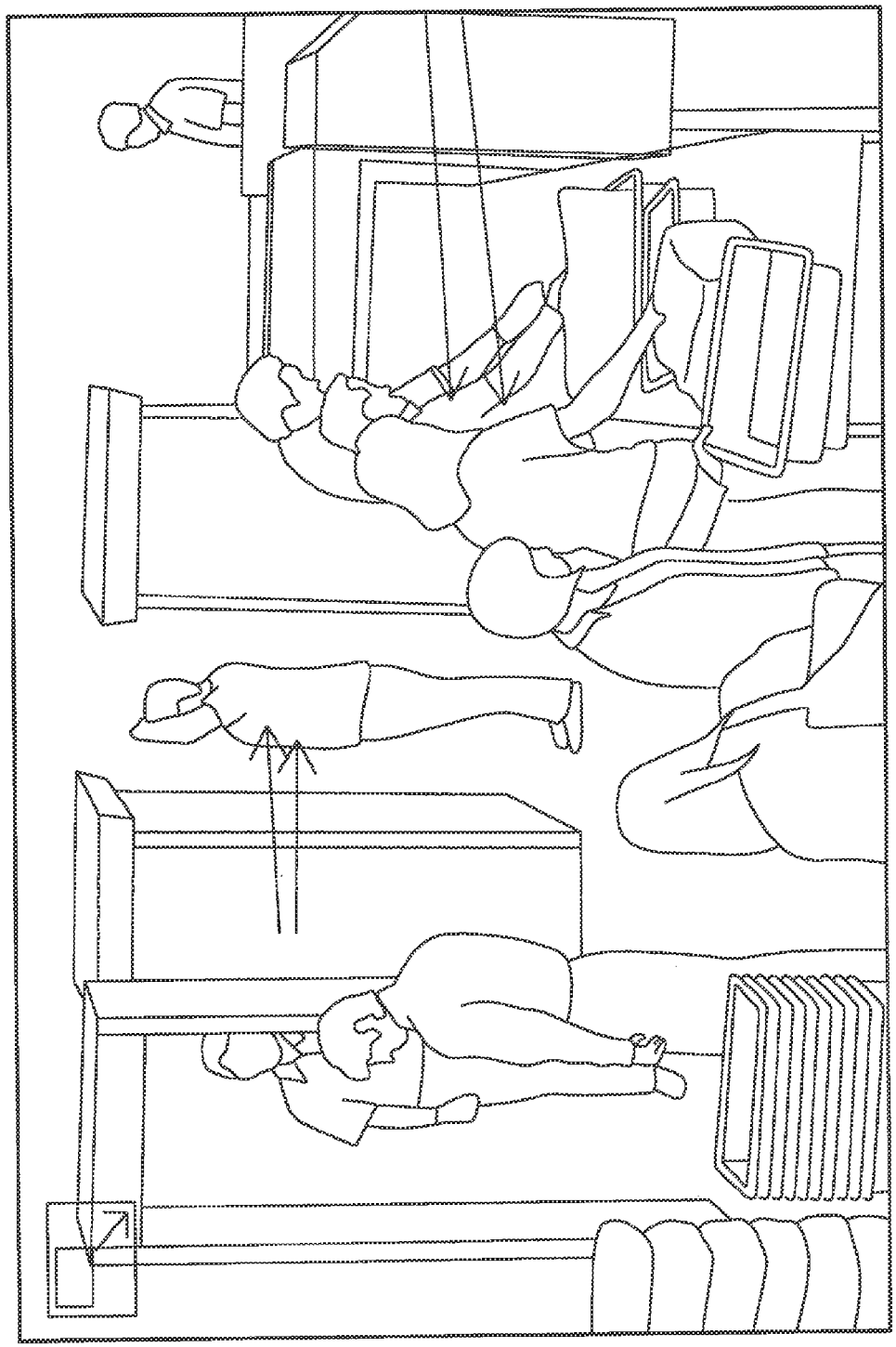
FIG. 3 is a pictorial representations of an exemplary application for an ultra-fast X-ray source (incoherent and/or X-ray laser) interrogation system in accordance with exemplary embodiments of the invention.

FIG. 3 shows a further embodiment of a stand-off ultra-fast X-ray source (incoherent and/or X-ray laser). X-ray laser interrogation system well suited for an airport passenger screening application. While conventional systems at security checkpoints have a limited ability to detect non-metallic explosives or other contraband, inventive ultra-fast X-ray source (incoherent and/or X-ray laser) interrogation systems are highly effective in detecting such materials with range gated pulsed X-ray detection. For example, as shown in FIG. 3 a person that may have a tapered non-metallic explosive taped well against stomach can be detected via range gated narrow beam interrogation.

Range gating directly addresses the challenges involved in achieving three-dimensional target profiling as a function of thickness or depth. As used herein, range gating refers to the transmission of a pulsed X-ray beam and collecting the signal returns in "bins" that correspond to the time at which they measured at the receiver. The bins can be directly related to the range at which the return signal originated. Therefore, return signals from a specific "range bin" can be conveniently isolated from all other returns. In particular, the return signal specific to the contents of target material concealed in a container can be isolated from returns due to the container walls or atmospheric scattering, thus eliminating the obscuring impact of these effects. Furthermore, range gating enables direct determination of the three-dimensional profile of a target material; narrower pulses translate into finer range resolution in the profile. Range gating obviates the infrastructure and multiple sources/detectors that are inherent in the tomography approaches currently in use, as well as the temporal delays of serial measurements.

However, conventional CW x-ray systems lack narrow pulses; and so, they do not support range gating. Furthermore, detection techniques for these x-ray sensors rely on temporally integrating the return signal, and do not attempt to range gate. Hence, they are subject to air transport effects which will degrade the fidelity of backscattered signal, especially those from low Z elements (C, N, O).

Range gating is established in radar at RF wavelengths, and in LIDARs/LADARs at optical wavelengths. These methods invoke range gating for determination of the range to the surface of a reflecting object. Range gating at x-ray and gamma ray wavelengths for efficient, three-dimensional profiling, in addition to the distance to an object, is new and unique.

Figure 4:
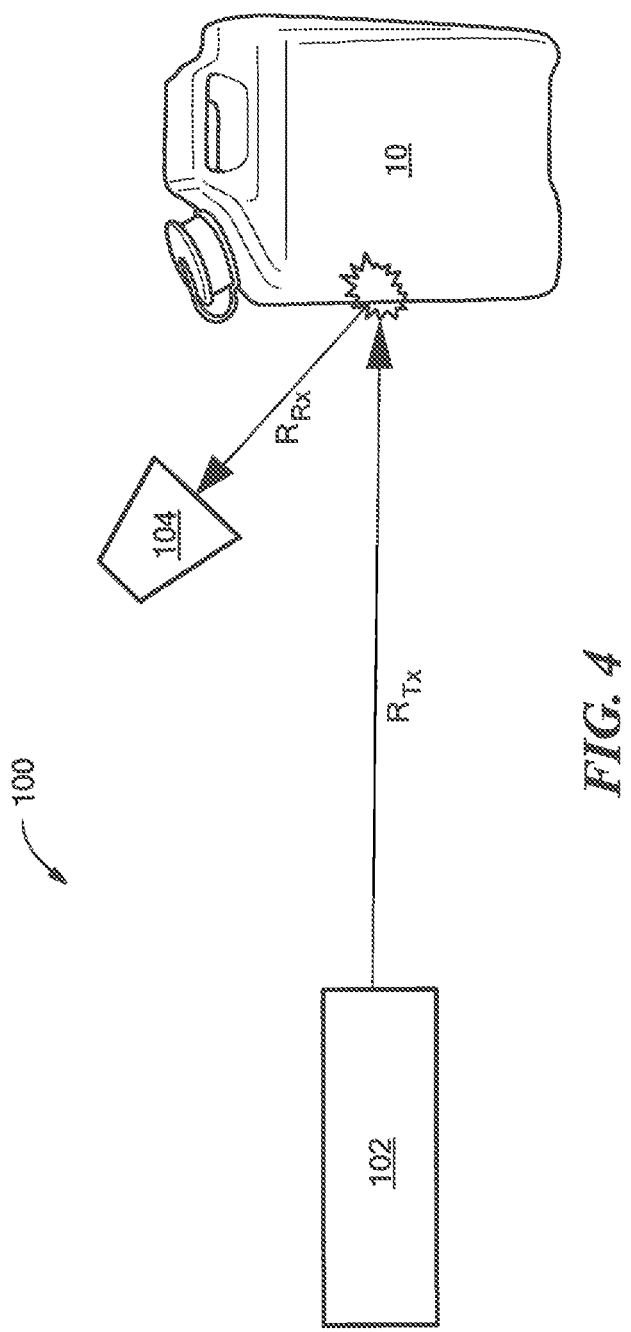
FIG. 4 is a schematic representation of an exemplary ultra-fast X-ray source (incoherent and/or X-ray laser) interrogation system in accordance with exemplary embodiments of the invention.

FIG. 4 shows an exemplary interrogation system 100 having an X-ray energy source 102, such as an ultra-fast pulsed X-ray transmitter, to irradiate a target 10, shown as a plastic can, and directly determine the elemental composition of a target material in the can from differential backscattering. An energy resolving X-ray detector(s) 104 detects photons emitted from the target in response to irradiation by the X-ray energy source. The detection can be range-gated from the pulsed energy source/target. In one embodiment, the energy source 102 comprises a coherent ultra-fast (sub picoseconds pulse duration) mean energy tunable X-ray source(s) to identify materials of interest. It is understood that longer pulses can be used to meet the needs of a particular application.

In another embodiment, an X-ray source having pulse durations that are consistent with the application can be used. Similarly, regarding photon energy, an ultra-fast X-ray source (incoherent and/or X-ray laser) can interrogate bulk material inside a container. In exemplary embodiments, an X-ray source can also have photon energies that are consistent with the application(s) and cover the range from XUV to hard X-rays.

In one particular embodiment, the target 10 is a container in which a material is located. In another embodiment, the target includes surface residue. It is understood that no direct contact with the target is needed.

It is understood that a wide variety of materials in a range of applications are contemplated. Exemplary applications include detection of explosive materials, hazardous materials, contraband, improvised explosive devices, and the like, at security checkpoints, airports, bus and train terminals etc. It is understood that exemplary embodiments of the invention are applicable to other classes of materials, such as commercial materials in applications, for example, quality control in packaging and shipping. In one embodiment, an ultra-fast X-ray source (incoherent and/or X-ray laser), illuminates a cargo shipping container to detect explosive materials. In another embodiment, an energy source illuminates vehicles for inspection at traffic checkpoints for example. In a further embodiment, an energy source illuminates luggage and people at the airport. Other applications will be readily apparent to one of ordinary skill in the art. Any contraband material with specific/unique X-ray back scattering signatures (Coherent Thompson scattering and Incoherent Compton scattering) can be identified and/or classified. FIG. 5 shows the elemental composition of exemplary explosive material as compared to common confusants showing a definitive difference in the relative ratios of C, N, and O.

Figure 6A:
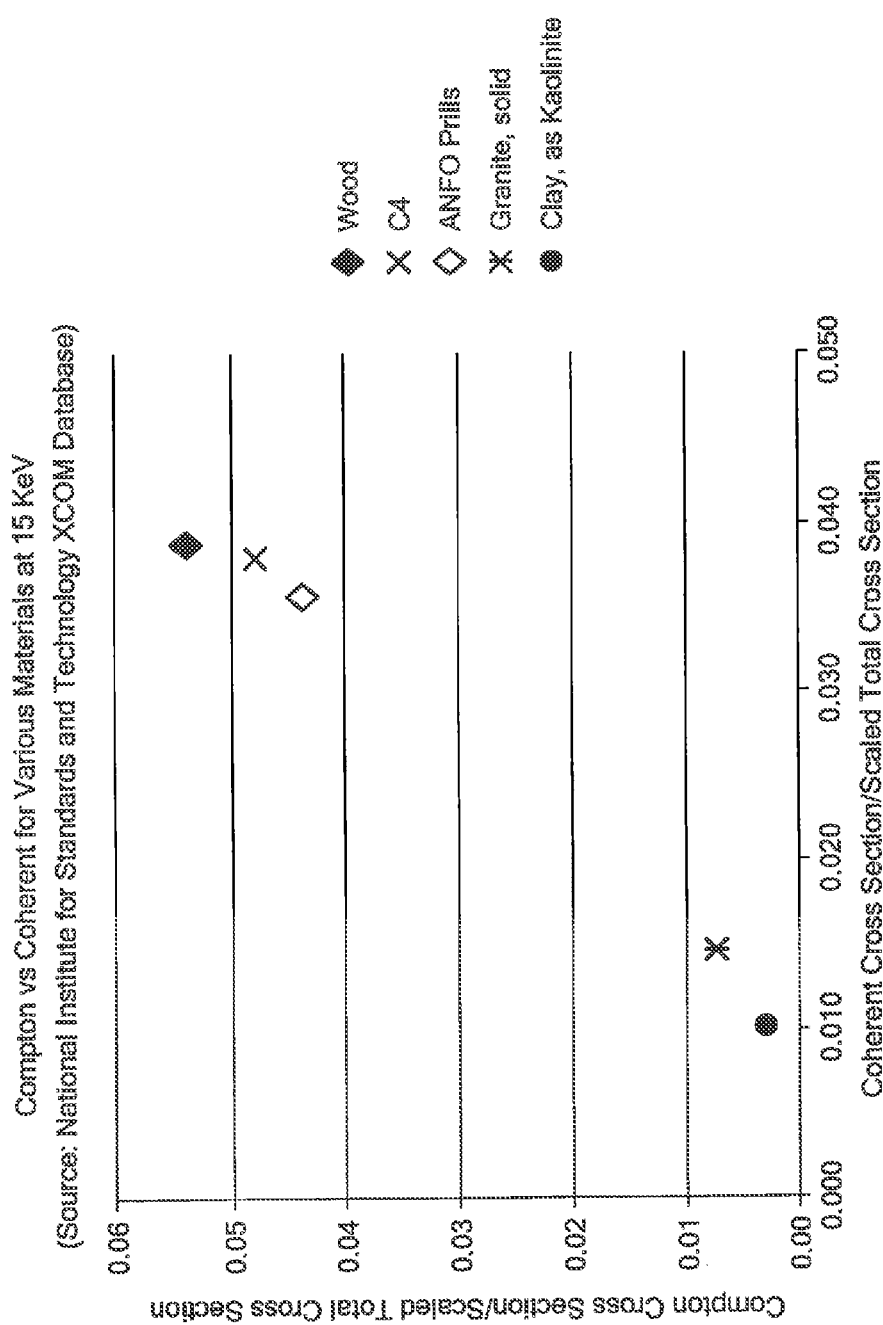
FIG. 6A is a graphical representation of Compton backscattering versus coherent backscattering for certain materials at 15 KeV.
Figure 6B:
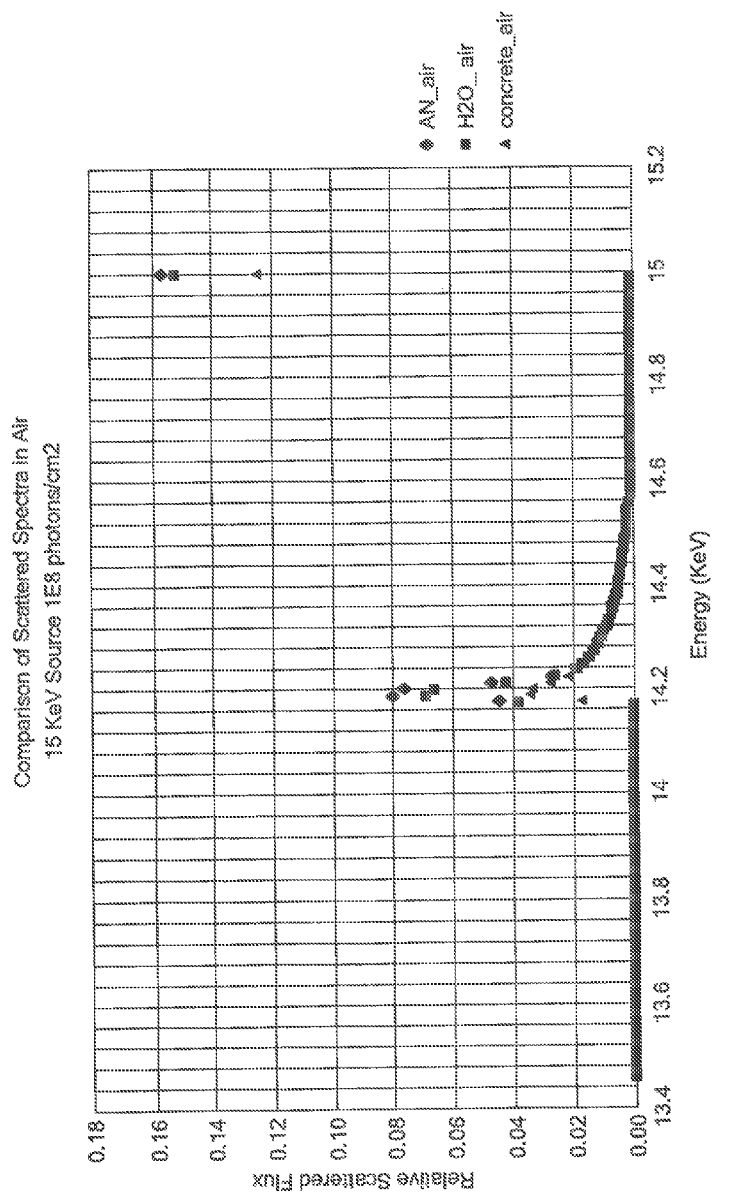
FIG. 6B is a graphical representation of a comparison of scattered spectra in air.

Preliminary modeling using industry accepted X-ray backscattering tool MCNPX (Monte Carlo N-Particle sXtended) indicates definitive Coherent and Incoherent scattering cross section differences between contraband/explosives and common confusants, as illustrated in FIGS. 6A and 6B. FIGS. 6A, B show MCNPX modeling based on cross sections compiled in the XCOM NIST data base: X-ray backscattering simulation utilizing weighted elemental composition indicate classification/identification of common explosives.

Detailed modeling at an array of X-ray photon energies provides a relative C, N, and O elemental composition enabled by energy dispersive X-ray detectors, as shown in FIG. 7. A priori knowledge (with reference photon energy distribution intensity measurement of each pulse) provides a known weighted intensity within each detector photon energy bin. Known expected relative backscattering cross section values within the corresponding photon energy bins enables the relative concentration measurements of C, N, O for solving three equations in three unknowns for a minimum of three frequency bins from analysis and processing of return signals.

Figure 8:
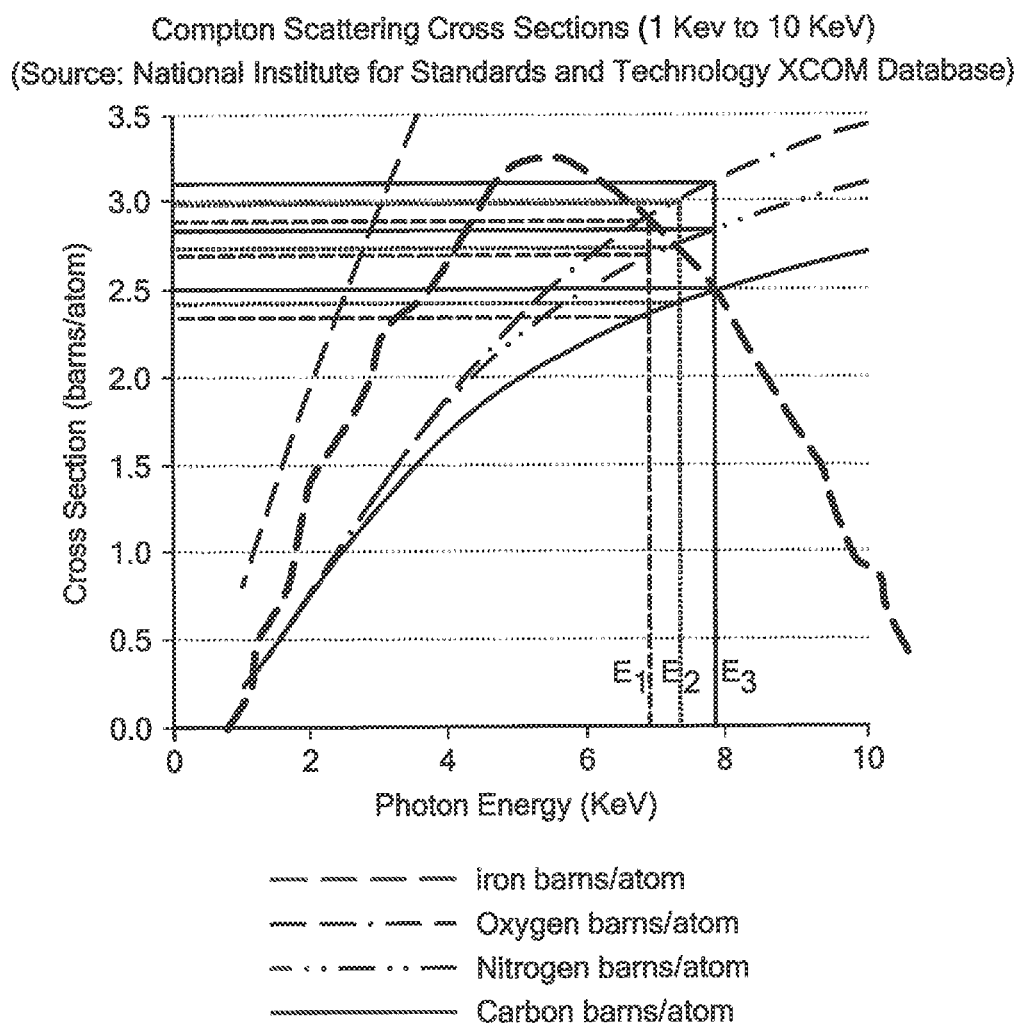
FIG. 8 is a graphical representation of Compton scattering cross sections for certain materials.

FIG. 8 illustrates the dispersion of the back scattering cross section responses of the key elements. At each different photon energy bin (defined by detector spectral resolution) the three elements have distinctly different cross section responses.

The expected signals—cumulative Compton and Coherent back scattered photons, $C_{cumulativeE_x}$, that the energy resolving detector will see at each energy bin, $E_{x_3}$, is given by following equations:

$$C_{cumulativeE_1} = \Sigma(C_{ironE_1} + C_{otherhighZelementbackgroundE_1} + \alpha_{j1}C_{CarbonE_1} + \alpha_{k1}C_{NitrogenE_1} + \alpha_{l1}C_{OxygenE_1}) \times I_{E_1} \times \eta_{airattenE_1}$$

$$C_{cumulativeE_2} = \Sigma(C_{ironE_2} + C_{otherhighZelementbackgroundE_2} + \alpha_{j2}C_{CarbonE_2} + \alpha_{k2}C_{NitrogenE_2} + \alpha_{l2}C_{OxygenE_2}) \times I_{E_2} \times \eta_{airattenE_2}$$

$$C_{cumulativeE_3} = \Sigma(C_{ironE_3} + C_{otherhighZelementbackgroundE_3} + \alpha_{j3}C_{CarbonE_3} + \alpha_{k3}C_{NitrogenE_3} + \alpha_{l3}C_{OxygenE_3}) \times I_{E_3} \times \eta_{airattenE_3}$$

where the weighting intensity coefficients expressed as $\alpha_{j,k,l,1-3}$, and:

$C_{ironE_x}$ is the Compton and Coherent cross section for iron at Energy $E_x$ $C_{CarbonE_x}$ is the Compton and Coherent cross section for Carbon a Energy $E_x$ $C_{NitrogenE_x}$ is the Compton and Coherent cross section for Nitrogen at Energy $E_x$ $C_{OxygenE_x}$ is the Compton and Coherent cross section for Oxygen at Energy $E_x$ $\eta_{airattenE_x}$ is the attenuation coefficient in air at x-ray photon energy, $E_x$ $C_{otherhighZelementbackgroundE_x}$ is the Compton and Coherent cross section contribution from other elements at Energy $E_x$ The detector 104 (FIG. 4) obtains information to enable analysis of differential backscattering at multiple energies with a given resolution defined by the detector. In one embodiment, differential backscattering is analyzed for multiple photon energies to enable measurement of ratios of carbon, nitrogen, and oxygen for the target material. The ratio information can be used to determine if explosive material is present, for example.

Figure 9:
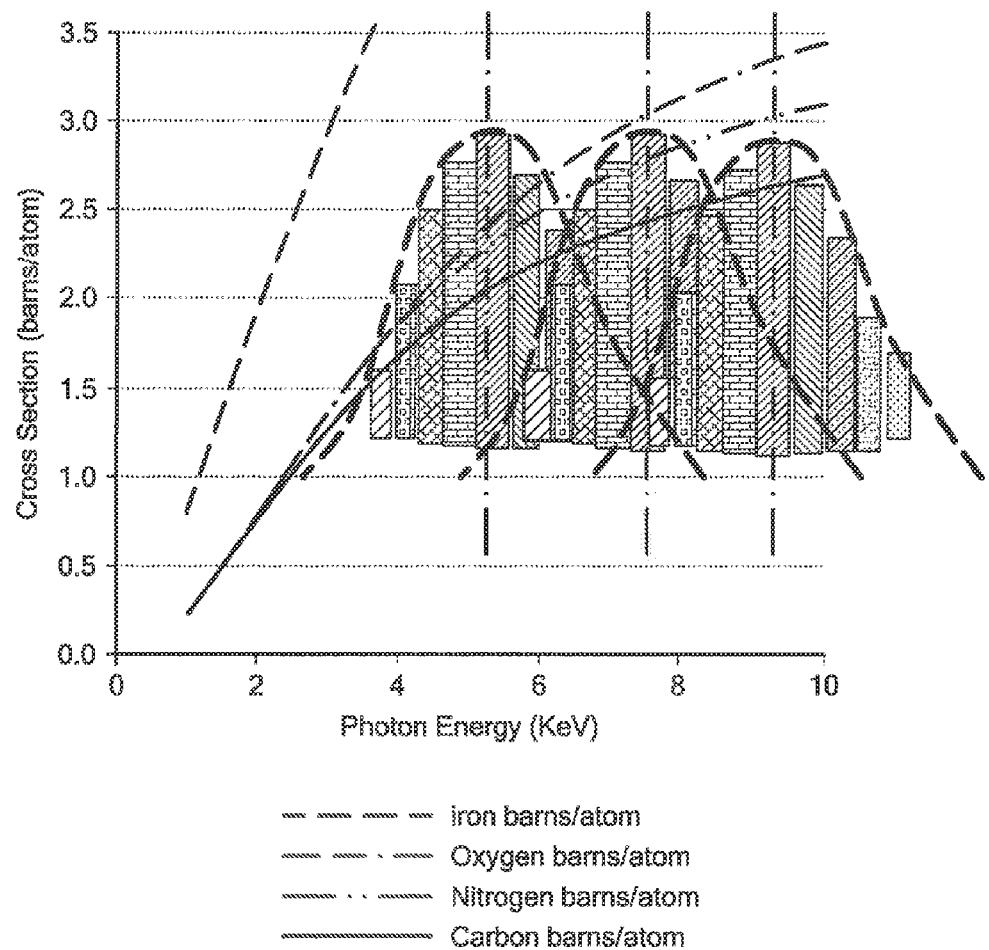
FIG. 9 is a graphical representation of Compton scattering cross sections for certain materials.

As one might expect energy dispersion by the medium—in essence "spill over" of signal from adjacent energy bins, an added discrimination to account for this can be achieved by interrogating the medium with tuned—different mean photon energy beam as illustrated in FIG. 9. Interrogation with different mean energy X-ray pulses with a priori knowledge of X-ray laser energy distribution utilizing a spectrally resolving detector outputs weighted spectrally integrated signals. Differential analysis can extract relative concentration of the three elements.

In one embodiment, desired X-ray signal detection of target of interest inside a bulk material beyond a container wall is achieved via range gating. Range gating is well known in the art and is commonly used in active range resolved LADAR (Laser Detection And Ranging) sensors. The time of flight cuing of the detector response can ignore "early"—arriving signals and detect signals/pulses arriving from a desired range via time gating. The short pulses of this ultra-fast X-ray source (incoherent and/or X-ray laser) approach enable this range resolution to be well under a cm.

In one embodiment, a DIAL (Differential Absorption LIDAR ((Light Detection And Ranging)) type approach is used where different mean peak energy X-ray pulses provide for a common path attenuation in order to decouple background signal contributions such as that due to elements having high atomic numbers, as illustrated in FIG. 9 (here shown as a much larger backscattering element and with its known signatures they can be subtracted out in signal processing). The ultra-fast X-ray source (incoherent and/or X-ray lasers) can be tuned to different mean photon energies, depending on the particular conops scenario.

Figure 10:
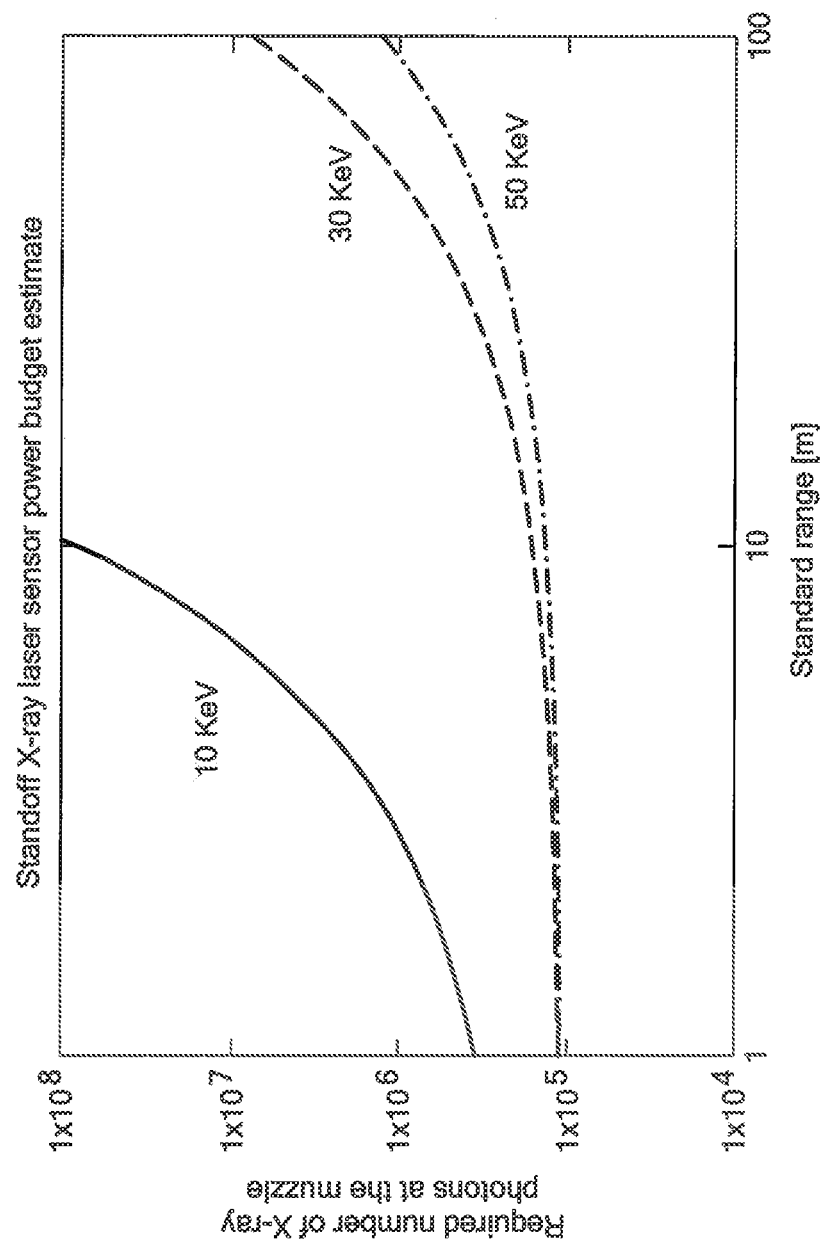
FIG. 10 is a graphical representation for an exemplary power budget for a required number of X-ray photons versus standoff range.

Differential Compton backscattering cross-sections are used for bulk material interrogation. Compton backscattering provides for X-ray interrogation at ranges governed by the overall attenuation in air, container wall attenuation and the attenuation of the bulk material backscatter attenuation. One scenario based on a 10, 30 and 50 keV X-ray laser illustrates the power budget needed as a function of standoff range shown in FIG. 10. The power budget for a given detector sensitivity and SNR drives required photons per pulse needed for different X-ray laser photon energies. This is primarily driven by the distributed attenuation in air which diminishes as the photon energy goes up.

Figure 11:
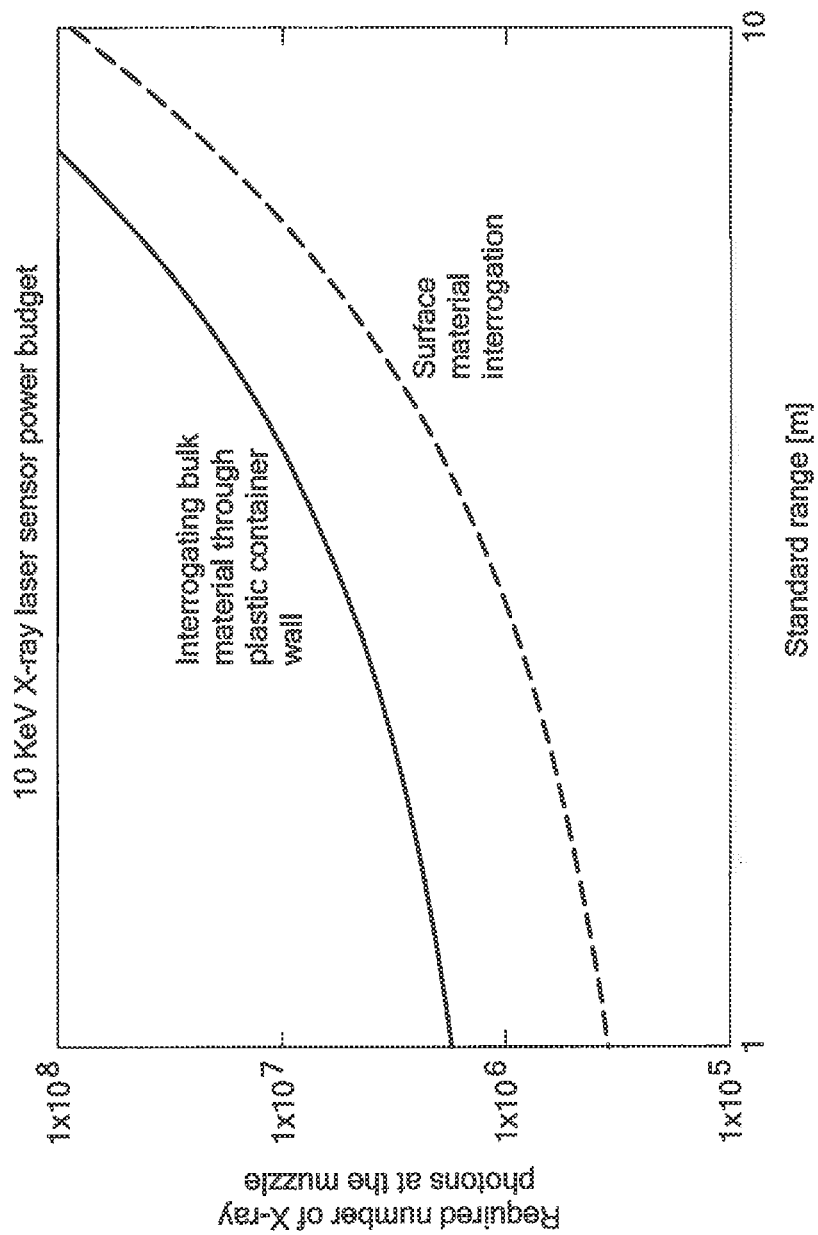
FIG. 11 is a graphical representation for an exemplary power budget for an ultra-fast X-ray source (incoherent and/or X-ray laser) interrogation system.

Even at 10 keV, the sensor can probe though common plastic container walls (such as polyethylene gasoline tanks/cans) with modest increase in needed photons or only slightly diminished stand-off range (if keeping required photon number per pulse constant), as illustrated in FIG. 11. The power budget estimate for a 10 keV laser sensor showing the air attenuation penalty only (red curve) as would be the case if one interrogates surface residue, and the scenario of bulk material interrogation though a common plastic can container wall (blue curve).

A 100 keV X-ray source has even lower air attenuation and can easily penetrate metal container walls for interrogating bulk materials in, for example, gas tanks. As is known in the art, Compton and Thompson (Incoherent and Coherent respectively) can scatter in a backward direction—hence "backscattering" or in the forward and side directions—"forward scattering." It is understood that exemplary embodiments of the invention can utilize backscattering and/or forward scattering.

As is known in the art, Compton scattering is a type of scattering that X-rays undergo in matter. The inelastic scattering of photons in matter results in a decrease in energy (increase in wavelength, $\lambda$) of an X-ray or gamma ray photon, called the Compton effect. Part of the energy of the X-ray is transferred to a scattering electron, which recoils and is ejected from its atom (which becomes ionized), and the rest of the energy is taken by the scattered photon. The amount the wavelength changes by is called the Compton shift.

Figure 12:
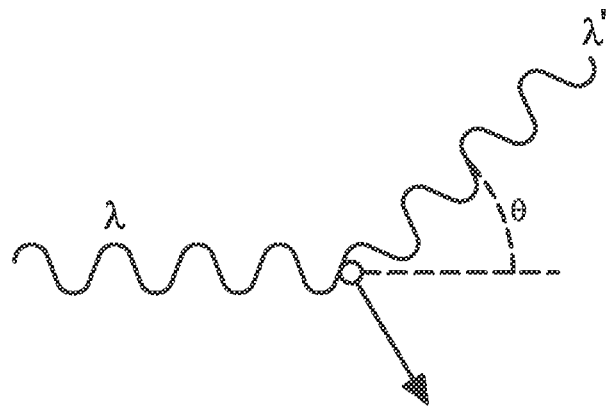
FIG. 12 is a schematic representation of the Compton backscattering process.

As shown in FIG. 12, a photon of wavelength $\lambda$ comes in from the left, collides with a target at rest, and a new photon of wavelength $\lambda'$ emerges at an angle $\theta$. When X-rays photons interact with atoms, the X-rays are scattered through an angle $\theta$ and emerge at a different wavelength related to $\theta$. The elastic (Thompson) and this inelastic) Compton signals are given in modeling results of FIG. 6.

The elemental composition of the target material can be determined by X-ray irradiation and detecting the Compton scattering. Elements having different atomic numbers can be detected.

X-ray interrogation of the target material does not activate the material as would be the case with neutrons and high energy Gamma rays, hence, more desirable for practical implementation. Relatively short pulse X-rays are typically desirable for minimal interference and radiation dosage to the target material.

In general, accelerator-type lasers are impractical for interrogating targets in accordance with exemplary embodiments of the invention. In addition to the cumbersome size and complexity (requiring cryogenic plants) of linear accelerators, it is a significant undertaking to tune the accelerator to a given frequency. That is, linear accelerators are not frequency agile, and thus, not practical for interrogating a target with multiple photon energies.

In exemplary embodiments of the invention, Compton Scattering based X-ray interrogation is achieved at relatively higher classes of photon energy. For example, at levels greater than about 100 keV X-rays penetrate metals significantly better than lower levels. At over 100 keV, the Compton effect may be dominant.

Exemplary embodiments of the invention and ultra-fast X-ray X-ray laser sensor rely on the unique features of laser beams: diffraction limited beam propagation which is governed by a diffraction angle:

$$\theta_{diff} = 2.44 \frac{\lambda}{D}$$

where D is the diameter of the laser beam/aperture. X-ray lasers having extremely short wavelengths will undergo a very low beam expansion with negligible spot size growth to even at 100 meters. This directionality enables the sensor to be utilized with high level of target resolution in a scanning mode implementation. With ultra-fast laser triggered incoherent X-ray pulsed sources, other collimation techniques using X-ray optics can be employed to reduce beam divergence and even focus at target.

Another feature of lasers is well-defined mean photon energy with a shape that can be approximated by a Gaussian distribution, unlike incoherent sources which form a monotonically decreasing continuum with no defined peaks. (The current X-ray lasers feature a fairly broad Gaussian like distribution with a full width half maximum equal to the peak values. This broad emission could be narrowed as the science of generating the table top x-ray sources progresses.) The mean energy of the X-ray laser can be "dialed in" at different values—hence giving this sensor frequency agility even if not real time/continuous tuning. In one embodiment, multiple X-ray laser emitters are used with different mean photon energies in order to effect the sensor modality described herein (as shown for example in FIG. 9).

Figure 13:
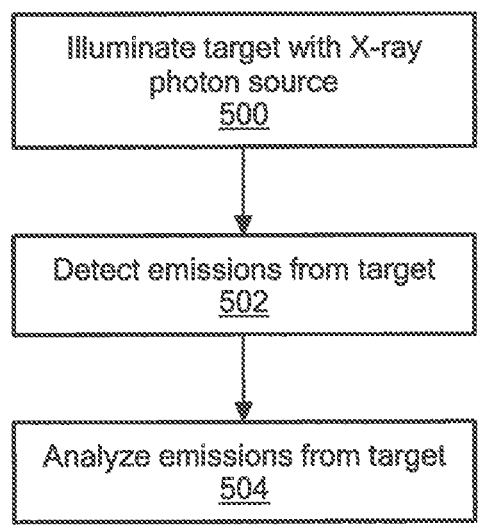
FIG. 13 is a flow diagram showing an exemplary sequence of steps to implement ultra-fast X-ray source (incoherent and/or X-ray laser) interrogation.

FIG. 13 shows an exemplary sequence of steps to provide ultra-fast X-ray source (incoherent and/or X-ray laser) interrogation in accordance with exemplary embodiments of the invention. In step 500, a pulsed, coherent X-ray photon source is directed to illuminate a target. In step, 502, one or more of photons, electrons and/or positrons emitted from the target, or transmitted through the target, are detected as a result of illumination of the target by the photon source. In step, 504, the detected photons, electrons and positrons are analyzed for characterizing a material forming at least part of the target.

In one embodiment, the material is identified as comprising an explosive material. The photon energies from the photon source can be at least 5 keV (kilo electron Volts) and/or photon pulses from the photon source can have pulse durations less than 10 picoseconds.

Exemplary embodiments of the invention provide a stand-off ultra-fast X-ray source (incoherent and/or X-ray laser) interrogation systems and methods that use highly directional X-ray pulses for remote sensing of target materials, which can be behind a barrier or within a container. In one embodiment, explosive compounds and/or elemental components of these compounds, such as carbon, nitrogen and oxygen are detected. In alternative embodiments, other target materials are of interest. By using relatively short pulse X-rays, e.g., picoseconds to hundreds of femtoseconds, the radiation dosage to the target material is relatively small so as to minimize damage to the target material and safe for accidental human exposure. Direct determination of the target material composition is achieved rather than indirect measurement of density and compound trace analysis, as in conventional systems.

Figure 14:
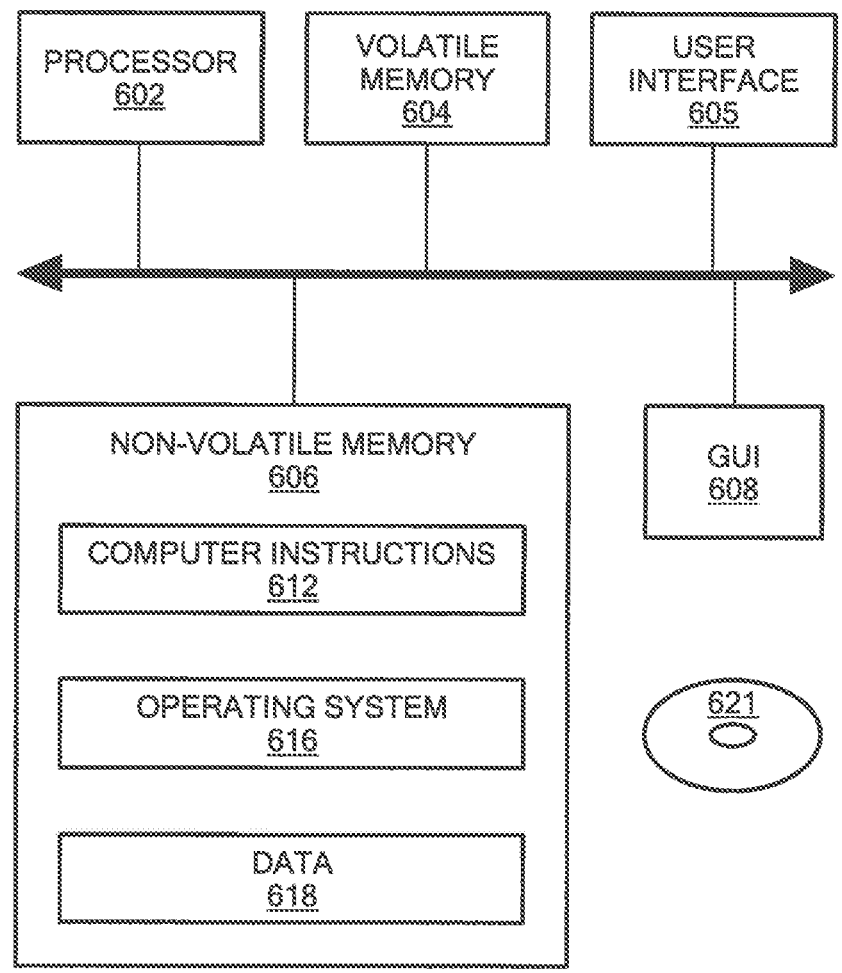
FIG. 14 is a schematic representation of an exemplary computer that can perform processing described herein.

FIG. 14 shows an exemplary computer 600 that can perform at least a portion of the processing described herein. The computer 600 includes a processor 602, a volatile memory 604, a non-volatile memory 606 (e.g., hard disk), a graphical user interface (GUI) 608 (e.g., a mouse, a keyboard, a display, for example) and an output device 605. The non-volatile memory 606 stores computer instructions 612, an operating system 616 and data 618. In one example, the computer instructions 612 are executed by the processor 602 out of volatile memory 604 to perform all or part of the processing described herein. An article 621 can comprise a computer-readable medium containing non-transitory stored instructions that enable the computer to perform processing.

Processing described herein is not limited to use with the hardware and software of FIG. 11; they may find applicability in any computing or processing environment and with any type of machine or set of machines that is capable of running a computer program. Processing may be implemented in hardware, software, or a combination of the two. Processing may be implemented in computer programs executed on programmable computers/machines that each includes a processor, a storage medium or other article of manufacture that is readable by the processor (including volatile and non-volatile memory and/or storage elements), at least one input device, and one or more output devices.

The system may be implemented, at least in part, via a computer program product, (e.g., in a machine-readable storage device), for execution by, or to control the operation of, data processing apparatus (e.g., a programmable processor, a computer, or multiple computers)). Each such program may be implemented in a high level procedural or object-oriented programming language to communicate with a computer system. However, the programs may be implemented in assembly or machine language. The language may be a compiled or an interpreted language and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network. A computer program may be stored on a storage medium or device (e.g., CD-ROM, hard disk, or magnetic diskette) that is readable by a general or special purpose programmable computer for configuring and operating the computer when the storage medium or device is read by the computer. Processing may also be implemented as a machine-readable storage medium, configured with a computer program, where upon execution, instructions in the computer program cause the computer to operate.

Having described exemplary embodiments of the invention, it will now become apparent to one of ordinary skill in the art that other embodiments incorporating their concepts may also be used. The embodiments contained herein should not be limited to disclosed embodiments but rather should be limited only by the spirit and scope of the appended claims. All publications and references cited herein are expressly incorporated herein by reference in their entirety.

What is claimed is:

1. A system comprising:
    an X-ray source for illuminating a target, the X-ray source comprising a plurality of transmitters each producing a different photon energy or mean photon energy, wherein photon energies from the X-ray source are between 1 keV (kilo-electron Volts) and 100 keV;
    a detector to detect one or more of photons, emitted from the target as a result of the target illumination by the X-ray source, wherein the photons are emitted from the material due to Compton scattering and/or coherent (Thomson) scattering; and
    a signal processor coupled to the detector to analyze the detected scattered photons and to perform range gating on the analyzed scattered photons for determining a three dimensional chemical compositional profile of the target.

2. The system according to claim 1, wherein the signal processor is configured to identify the material as comprising an explosive material.

3. The system according to claim 1, wherein photon pulses from the transmitter X-ray source have pulse durations less than 10 picoseconds.

4. The system according to claim 1, wherein the ultra-fast X-ray source comprises an ultra-fast laser triggered x-ray tube and/or an X-ray laser to generate highly directional low divergence beams.

5. The system according to claim 1, wherein the target is located behind a barrier.

6. The system according to claim 1, wherein the target is within a container.

7. The system according to claim 1, wherein the photons are emitted from the material due to reflection, refraction, diffraction, Compton scattering, coherent scattering, and/or fluorescence.

8. The system according to claim 1, wherein the X-ray source comprises an incoherent and/or X-ray laser.

9. The system according to claim 1, wherein at least some of the photons from the X-ray source are transmitted through the material.

10. The system according to claim 1, wherein the detector is fixed on or immediately adjacent to the X-ray source to provide a monostatic LADAR configuration.

11. The system according to claim 1, wherein the detector is fixed at a location that is remote from the X-ray source to provide a bistatic/multistatic LADAR configuration.

12. The system according to claim 1, wherein the detector is movable.

13. The system according to claim 1, wherein the signal processor is configured to perform range gating on the detector output for isolating signal return from the target and/or enabling three dimensional mapping/imaging of the target.

14. The system according to claim 1, wherein a beam from the X-ray source is directed at a specific location on the target for spot interrogation at a standoff distance.

15. The system according to claim 1, wherein a beam from the X-ray source is scanned to interrogate a target area.

16. A method, comprising:
directing an X-ray source to illuminate a target, the X-ray source comprising a plurality of transmitters each producing a different photon energy or mean photon energy, wherein photon energies from the X-ray source are between 1 keV (kilo-electron Volts) and 100 keV;
detecting one or more of photons emitted from the target as a result of illumination of the target by the X-ray source, wherein the photons are emitted from the material due to Compton scattering and/or coherent (Thomson) scattering;
analyzing the detected scattered photons; and
performing range gating on the analyzed scattered photons to determine a three dimensional chemical compositional profile of the target.

17. The method according to claim 16, further including identifying the material as comprising an explosive material.

18. The method according to claim 16, wherein the photons are emitted from the material due to reflection, refraction, diffraction, Compton scattering, coherent scattering, and/or fluorescence.

19. The system of claim 1 wherein the X-ray source is an ultra-fast X-ray source having an ultra-short pulse emission and a substantially non-divergent, diffraction limited, highly directional beam.

20. The system of claim 19 wherein the target has dimensions such that it can be worn by a person.

* * * * *